United States Patent [19]

Brendling

[11] Patent Number: 4,500,314
[45] Date of Patent: Feb. 19, 1985

[54] COLLAPSIBLE URINAL DROP COLLECTOR APPLICATOR

[76] Inventor: Lennart I. Brendling, Volmvägen 10, S-175 43 Järfälla, Sweden

[21] Appl. No.: 346,032
[22] PCT Filed: Jun. 10, 1981
[86] PCT No.: PCT/SE81/00174
§ 371 Date: Jan. 21, 1982
§ 102(e) Date: Jan. 21, 1982
[87] PCT Pub. No.: WO81/03609
PCT Pub. Date: Dec. 24, 1981

[30] Foreign Application Priority Data

Jun. 11, 1980 [SE] Sweden .................. 8004355
Jun. 11, 1980 [SE] Sweden .................. 8004356

[51] Int. Cl.³ .................................. A61F 5/44
[52] U.S. Cl. ...................... 604/346; 604/347; 604/349; 4/144.1; 4/144.3
[58] Field of Search ............. 604/317, 346, 347, 349, 604/351, 352; 128/760, 767; 4/144.1, 144.2, 144.3, 144.4

[56] References Cited

U.S. PATENT DOCUMENTS

| | | | |
|---|---|---|---|
| 3,403,410 | 10/1968 | Benzel et al. | 604/350 |
| 3,403,682 | 10/1968 | McDonell | 604/352 |
| 3,660,033 | 5/1972 | Schwartz | 128/767 |
| 3,830,107 | 8/1974 | Linzer et al. | 128/767 |
| 3,964,111 | 6/1976 | Packer | 604/327 |
| 4,002,276 | 1/1977 | Poncy et al. | 223/111 |
| 4,230,115 | 10/1980 | Waltz, Jr. et al. | 604/349 |
| 4,239,044 | 12/1980 | Pavlinch | 604/352 |
| 4,284,079 | 8/1981 | Adair | 604/349 |
| 4,453,938 | 6/1984 | Brendling | 604/346 |

FOREIGN PATENT DOCUMENTS 365183  4/1922  Fed. Rep. of Germany .

Primary Examiner—C. Fred Rosenbaum
Assistant Examiner—J. L. Kruter
Attorney, Agent, or Firm—Schroeder, Siegfried, Vidas & Arrett

[57] ABSTRACT

A device to facilitate putting an elastic envelope (1) on a part projecting from a human body, e.g. putting a urinal drop collector onto a penis, consists of a casing (4) with two flexible side walls (5, 6) connected to each other along at least two of their side edges (5a, 6a; 5b, 6b) and with at least one opening (8) between two other side edges of the walls. The envelope is at least partially enclosed between the walls (5, 6) and its portion provided with an opening (2) is removably attached to said opening (8). By pressing the mutually connected side edges towards each other the opening (8) is enlarged between the walls, the opening of the envelope also being enlarged. The casing (4) is substantially flat when it is not used, and the space between it and the envelope (1) is airtight, whereby, when the opening (8) between the walls is extended, the portion of the envelope situated inside the casing is enlarged so that the envelope can be put onto part of the human body.

2 Claims, 7 Drawing Figures

COLLAPSIBLE URINAL DROP COLLECTOR APPLICATOR

TECHNICAL FIELD

The present invention relates to a device for facilitating putting an elastic envelope onto a part projecting from the human body, and a method of expanding the cross section of the envelope. The invention is particularly utilisable in conjunction with a condom-like urinal drop collector connected to a urinal collection bag and fixable onto a penis.

BACKGROUND ART

To fix a urinal drop collector onto a penis a fixing strip has so far been provided which has adhesive on both sides, or a latex emulsion brought round the penis has been used, after which the urinal drop collector has been rolled up onto the penis by hand to become affixed thereto.

The disadvantages with this method are that (a) two work operations are required for the application of the collector, namely one for arranging the adhesive and another for applying the collector, (b) the adhesive does not adhere to the collector around the whole of its inner periphery, especially if the collector has a larger cross section than the penis, whereby urine can pass out between the penis and the collector and (c) difficulties occur in applying the collector in the proper position, especially if the penis is retracted or if only one hand can be used to put the collector on, e.g. if a person suffers from rheumatism, with consequently reduced mobility in the fingers.

A device has also been developed, comprising a stiff tube surrounding the urinal drop collector, one open end of which removably retains the stretched-out opening portion of the elastic collector. A piston is arranged at the other end of the tube, and on movement away from said opening removes the air in the space between the inside of the tube and the outside of the collector so that the cross section of the latter is expanded and becomes greater than that of the penis. The tube with the expanded collector can subsequently be moved over the penis, and the piston moved towards said opening so that air is introduced in said space once again, the cross section of the collector then diminishing and enclosing the penis. The tube is then released and removed from the collector which is then retained on the penis by means of sticky tape attached to the penis before the collector is put on.

The primary drawbacks with this device are that the tubular portion at the front end of the urinal drop collector must be sealed off for the device to function at all, and this enclosure must be opened by clipping off a piece of the tubular portion before the collector is connected to a urine collection bag, that the device is voluminous, complicated and expensive, that several work operations must be carried out before the collector is correctly placed and that the seal between the penis and drop collector may be incomplete, since the sticky tape is put on the penis before the collector.

DISCLOSURE OF INVENTION

The object of the present invention is to provide a device to facilitate putting on the elastic envelope and correctly placing it on the penis and to improve the seal between the latter and the envelope, as well as a method of enlarging the cross section of this envelope. This object is achieved by the invention having been given the characterizing features disclosed in the claims.

BEST MODE FOR CARRYING OUT THE INVENTION

Figure 5:
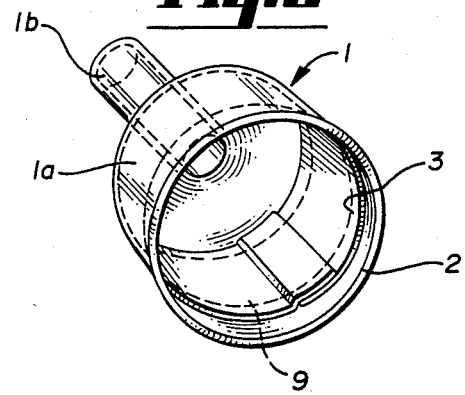
FIG. 5 is a perspective view of a urinal drop collector particularly adapted for use together with the devices illustrated in FIGS. 1 and 3.

A urinal drop collector 1 is shown in FIG. 5 and consists of an elastic tubular envelope 1a and an elastic tube 1b communicating with the envelope and integral therewith, the tube 1b being intended for connection to a conventional urine collection bag (not shown). The end of the envelope 1a facing away from the tube 1b is provided with an opening 2, and its edge is rolled over or folded over on the outside of the envelope. An elastic adhesive agent 9 is applied on the inside of the envelope somewhat inside the opening 2, the adhesive forming a closed ring round the inner periphery of the envelope and is covered by a strip-off membrane 3 which is first removed in conjunction with putting the collector onto a penis.

To facilitate putting the collector onto a penis, there is provided in accordance with the invention a device consisting, in a first embodiment illustrated in FIGS. 1 and 2, of a casing-like member, hereinafter called "casing" and denoted by the numeral 4. The casing 4 is tubular and comprises two substantially triangular walls 5 and 6 made from flexible plastics, which are mutually connected along side edges 5a, 6a and 5b, 6b, respectively. Each mutually attached pair of side edges can form a weakened zone to facilitate flattening the casing, or they can have the same thickness as the walls 5, 6 and thus constitute an unnoticeable portion thereof. Openings 7 and 8 are formed between the mutually unconnected side edges, the outmost portion of the tube 1b and the portion of the envelope 1a surrounding the opening 2 being foldable over said openings such that these portions engage against the edges of the openings 7, 8 and against the outsides of the walls 5 and 6 to which they are thereby removably connected in the manner illustrated in FIG. 1.

Figure 1:
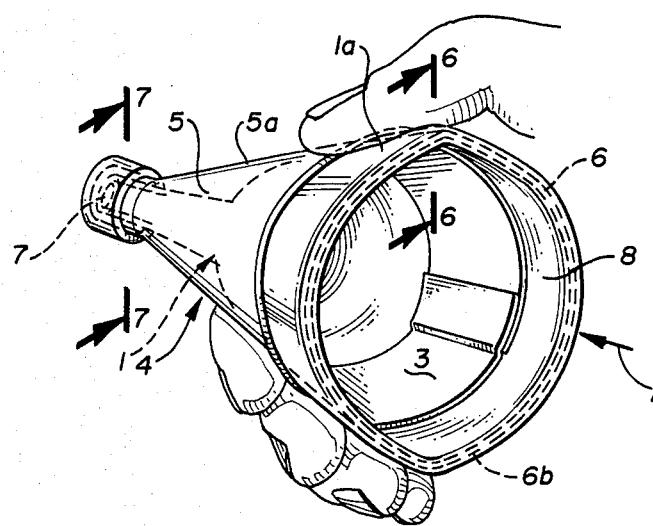
FIG. 1 is a perspective view of a first embodiment of a device in accordance with the invention in the position of use.
Figure 2:
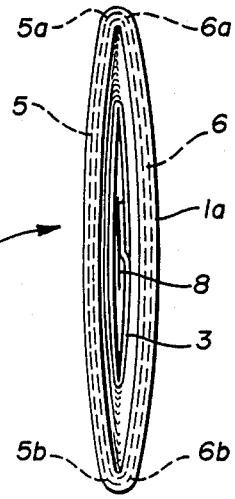
FIG. 2 is an end view seen in the direction of the arrow A in FIG. 1 of the device according to FIG. 1 in a position before use.
Figure 6:
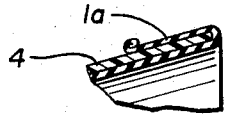
FIG. 6 is a fragmentary sectional view taken along lines 6—6 of FIG. 1.

When the device in accordance with the invention is in use, the casing 4 and the collector 1 partially enclosed therein as described above, are substantially flat, which is apparent from FIG. 2. When the device is to be used, the side edges 5a, 6a and 5b, 6b of the walls 5 and 6 are pressed with the fingers of one hand towards each other at a point near the opening, in a manner illustrated in FIG. 1, such that the casing is expanded and is substantially given the shape of a hollow cone, the opening 8 also expanding and obtaining a substantially circular or oval shape, which is also illustrated in FIG. 1. Since the space between the inside of the casing 4 and the outside of the collector 1 in the flat condition of casing and envelope is very small and furthermore airtight, which is because the portions 1a and 1b of the collector 1 are folded over the edges of the openings 7 and 8 and resiliently press and seal against said edges and against the outside of the walls 5 and 6, the portion of the elastic envelope 1a of the collector close to the tube 1b will be expanded and the envelope will therefore assume the shape shown in FIG. 1. The reason for the envelope 1a expanding substantially along the whole of its length is that the amount of air enclosed between the envelope and casing on urging the casing into conical shape is moved to the area outside the tube 1b, a sub-pressure being formed between the envelope 1a and the casing, said sub-pressure causing the envelope to be forced against the inside of the casing by atmospheric pressure.

The strip of membrane 3 covering the adhesive agent 9 on the inside of the envelope 1a is now easily accessible and can be removed. Removal is facilitated by the membrane being partially released from the adhesive 9 on the expansion of the envelope 1a, since a relative movement occurs between it and the membrane during expansion. The expanded collector 1 partially enclosed in the casing 4 is thereafter moved over the penis until the ring of adhesive 9 has passed over the glans, pressure against the side edges 5i a, 6a, 5b, 6b beig then eased and the walls 5 and 6 moved towards each other until the inside of the envelope 1a, and thereby the adhesive, comes into engagement against the penis. The walls 5 and 6 can now be lightly pressed towards each other to increase the pressure against the penis so that the adhesive 9 fastens against it. The portion of the envelope 1a facing away from the tube 1b can then be rolled off the edge round the opening 8 and the outer portion of the tube 1b can be rolled off the edge round the opening 7, thus introducing air into the space between the casing 4 and the collector 1, the cross section of the envelope 1a then diminishing to cause the envelope to surround the penis. The casing 4 can then be removed from the collector. By subsequently squeezing the envelope 1a against the penis in the area of the adhesive 9, not only does the inside of the envelope adhere to the penis but the surfaces on the inside of the envelope which do not come into contact with the penis due to the fact that the cross section of the envelope can be greater than that of the penis, can also adhere to each other, whereby no air or urine-passing channels 12 can be formed between penis and envelope. The tube 1b is finally connected to a urine collection bag in a conventional manner.

Figure 3:
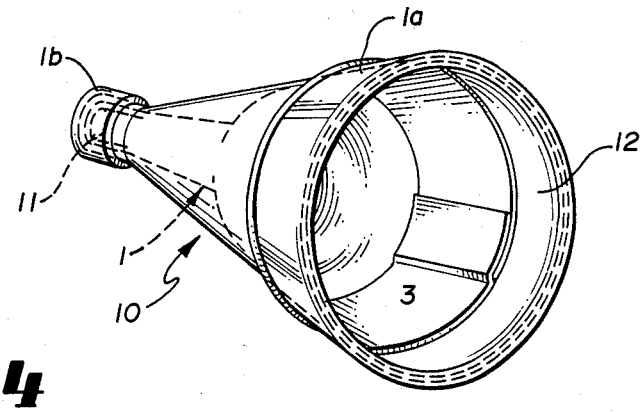
FIG. 3 is a perspective view of a second embodiment of a device in accordance with the invention.
Figure 7:
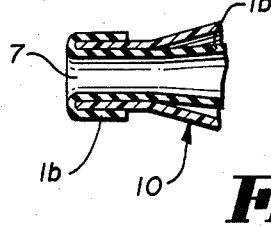
FIG. 7 is a vertical sectional view taken along line 7—7 of FIG. 1.
Figure 4:
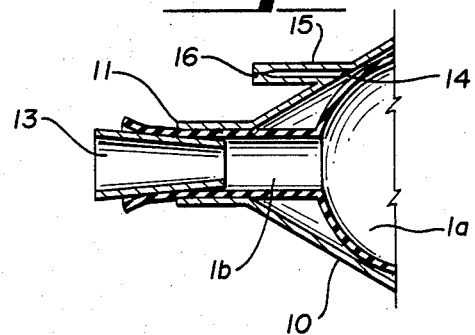
FIG. 4 is a sectional side view of a modified portion of the device in FIG. 3.

In a modification of the device illustrated in FIG. 1, the opening 7 as well as the tube 1b can be closed, and the closed end of the tube situated inside the space between the walls 5 and 6, whereby the space between the inside of the casing 4 and the outside of the urinal drop collector 1 will be airtight in this embodiment as well. The device thus functions in the same way as the one described above. An advantage with the embodiment modified in this way is that the operation of folding the outmost portion of the tube 1b round and away from the edge surrounding the opening 7 is dispensed with. A disadvantage is, however, that the closed end of the tube 1b must be clipped off before the urinal drop collector is connected to a urine collection bag. The device in a second embodiment according to the invention illustrated in FIGS. 3 and 4 comprises an elastic funnel-shaped plastics tube 10 open at both ends, having a circular opening 11 and a larger circular opening 12, over the edges of which the outermost portion of the tube 1b and the portion surrounding the opening 2 of the envelope 1a, respectively, can be folded so that these portions removably and sealingly engage against the edges of the openings 11, 12, and against the outside of the tube 10 in the mode illustrated in FIG. 3. Instead of folding the outmost portion of the tube 1b over the edge of the opening, this portion can be permitted to stick out of the opening 11, whereby a preferably hollow, somewhat conical plug 13 is inserted in the elastic tube 1b so that the walls thereof are sealingly urged against the opening 11. This embodiment is indicated in FIG. 4. In both these last-mentioned embodiments the seal between the opening 11 and the tube 1b ensures that air can pass through the collector between both its open ends, which is of importance when putting the collector onto the penis.

Before the device in accordance with the invention is used, there is a relatively large amount of air between the inside of the tube 10 and the outside of the drop collector 1, resulting in that the envelope 1a has a relatively small cross section along the whole of its length, with the exception of the part of the envelope connected to the opening 12. Before the collector is put onto the penis, the cross section of the envelope must be increased so that it will be greater than the cross section of the penis in the vicinity of the tube 1b also. A suction means is used to increase the cross section, this means being connected in a suitable way to the space between the tube and the collector in the area outside the tube 1b, where the distance between said wall and the collector is greatest. When the suction means is operated, air is sucked out of said space, the envelope 1a expanding so that it contacts the inside of the tube and its shape thus conforming thereto in the way illustrated in FIG. 3.

Some suitable known means can be used to remove air from the space between the tube 10 and envelope 1a. In an embodiment indicated in FIG. 4, a third opening 14 can be made in the wall of the tube 10, and a small tube 15, possibly provided with a non-return valve 16, can be connected to said third opening. This tube can be connected to a suction pump such as an injection syringe without a needle, or air can be sucked from said space with the aid of the mouth. The non-return valve 16 prevents air being re-introduced into the space in the latter case.

The strip-off membrane covering the adhesive 9 on the inside of the envelope 1a is taken away after the envelope has been expanded. The expanded collector 1 enclosed in the tube 10 is thereafter put over the penis and the walls of the tube pressed against the penis so that the adhesive 9 fastens to it, after which the portion of the tube 1a facing away from the tube 1b is rolled off the edge around the opening 12 and the outermost portion of the tube 1b is rolled off the edge round the opening 11, air thereby being introduced into the space between the tube 10 and the collector 1, the cross section of the envelope 1a thus being diminished and caused to surround the penis. The tube 10 can subsequently be removed from the collector. By afterwards squeezing the envelope 1a against the penis in the area of the adhesive 9, not only does the inside of the envelope adhere to the penis, but the surfaces on the inside of the envelope which do not come into engagement with the penis adhere to each other, whereby no air or urine-passing channels are formed between penis and envelope. The tube 1b is finally connected to a urine collection bag conventionally.

The invention is naturally not limited to the embodiments described above and shown on the drawings, but can be modified in different ways. Accordingly, the tube 11 can, for example, have a shape not conforming to the funnel shape shown in FIG. 3, and could be cylindrical in a conceivable embodiment. Neither is the device in accordance with the invention limited to use as an aid for putting a urinal drop collector on a penis but can also be used for such tasks as facilitating putting on a condom on a handicapped person, or putting a latex glove on a surgeon's hand. In both these cases, similar to the case for the described embodiment where the tube 1b is closed, the device in accordance with the invention does not have an opening corresponding to the opening 7 or 11. The invention is thus only restricted by what is disclosed in the claims.

I claim:

1. A device for facilitating the connection of a urinal drop collector to a penis comprising:
   (a) a normally flat tubular casing having inner and outer surfaces and being comprised of a pair of opposed, flexible, substantially identical, generally triangular walls, each of which has a pair of side edges juxtapositioned to the corresponding side edges of the other and flexibly connected thereto and having a relatively large open upper end portion and a relatively small open tubular lower end portion; and
   (b) an open-ended elastic tubular envelope removably connected to said casing and extending therethrough throughout the length thereof, said envelope having one end portion thereof stretched outwardly over and around the exterior of said lower end portion of said casing and having its opposite end portion stretched outwardly over and around said upper end portion of said casing, each in air-tight sealing relation and thereby sealing the area between said casing and said envelope in air-tight relation, whereby upon said pairs of side edges of said casing being pressed toward each other, said upper end portion of said casing will assume a conical shape and said envelope will expand and extend in close-fitting relation along the inner surface of said casing along a substantial portion of the entire length of said envelope.

2. A device for facilitating the connection of an elastic tubular envelope to a part projecting from the human body comprising:
   (a) a normally flat tubular casing having inner and outer surfaces and being comprised of a pair of opposed, flexible, substantially identical, generally triangular walls, each of which has a pair of side edges juxtapositioned to the corresponding side edges of the other and flexibly connected thereto and having a relatively large open upper end portion and a relatively small closed lower end portion;

and
   (b) an elastic tubular envelope removably connected to said casing and extending therethrough substantially throughout the length thereof, said envelope having one end portion thereof closed and interior of said lower end portion of said casing and having its opposite end portion open and stretched outwardly over and around said upper end portion of said casing in air-tight sealing relation and thereby sealing the area between said casing and said envelope in air-tight relation, whereby upon said pairs of side edges of said casing being pressed toward each other, said upper end portion of said casing will assume a conical shape and said envelope will expand and extend in close-fitting relation along the inner surface of said casing along a substantial portion of the entire length of said envelope.

* * * * *